(12) United States Patent
Green

(10) Patent No.: US 6,785,926 B2
(45) Date of Patent: Sep. 7, 2004

(54) MECHANICALLY-DRIVEN TOOTHBRUSH WITH IMPROVED BRUSHING ACTION

(76) Inventor: Carl Green, 485 Dartmouth Ave., San Carlos, CA (US) 94070

( * ) Notice: Subject to any disclaimer, the term of this patent is extended or adjusted under 35 U.S.C. 154(b) by 272 days.

(21) Appl. No.: 10/140,723

(22) Filed: May 9, 2002

(65) Prior Publication Data

US 2003/0208863 A1 Nov. 13, 2003

(51) Int. Cl.[7] .............................................. A46B 13/02
(52) U.S. Cl. .......................... 15/22.1; 15/22.4; 403/373
(58) Field of Search ................................ 15/22.1, 22.4, 15/22.2, 23, 28; 403/373, 374.1, 374.2, 365, 366

(56) References Cited

U.S. PATENT DOCUMENTS

| | | | | |
|---|---|---|---|---|
| 2,201,190 A | * | 5/1940 | Mastrud .................... | 15/22.4 |
| 2,827,794 A | * | 3/1958 | Weimersheimer ............ | 74/127 |
| 2,912,706 A | * | 11/1959 | Gerecke et al. .............. | 15/22.4 |
| 3,088,148 A | * | 5/1963 | Moret ......................... | 15/22.1 |
| 3,104,405 A | * | 9/1963 | Perrinjaquet ................ | 15/22.1 |
| 3,233,265 A | * | 2/1966 | Hartmann ................... | 15/22.1 |
| 3,369,265 A | * | 2/1968 | Halberstadt ................. | 15/22.1 |
| 3,400,417 A | * | 9/1968 | Moret ......................... | 15/22.1 |
| 3,588,936 A | * | 6/1971 | Duve .......................... | 15/22.1 |
| 3,851,984 A | * | 12/1974 | Crippa ..................... | 403/322.4 |
| 4,506,400 A | * | 3/1985 | Klein .......................... | 15/22.1 |
| 5,613,258 A | | 3/1997 | Hiltfinger et al. ............ | 15/22.1 |
| 5,842,249 A | * | 12/1998 | Sato ........................... | 15/167.2 |
| 5,974,615 A | | 11/1999 | Schwarz-Hartmann et al. ........... | 15/22.1 |

* cited by examiner

Primary Examiner—Gary K. Graham

(57) ABSTRACT

A mechanically-driven toothbrush consists of a handle, which contains a driving motor with a conversion mechanism, and a toothbrush attachment removably connectable to the output shaft of the conversion mechanism. The handle with the conversion mechanism and the drive motor may comprise a standard, commercially produced unit with the output end of the conversion mechanism performing alternating rotary movements. The toothbrush attachment is made in the form of a conventional toothbrush head without any angular transmission. The tail of the head is connected with the output end of the conversion mechanism by a coupling, which has a locking element for engagement with an appropriate connection element on the output end of the conversion mechanism. The connection portion is covered by a protective sleeve that can be removably connected to the front end of the handle. In operation, the user moves the toothbrush up and down in the vertical directions of the teeth. Efficient removal of the plaque from the spaces between the teeth is achieved due to the fact that motions of the bristles imitate motions of a toothpick when the latter is used for poking the plaque from the intertooth spaces.

3 Claims, 4 Drawing Sheets

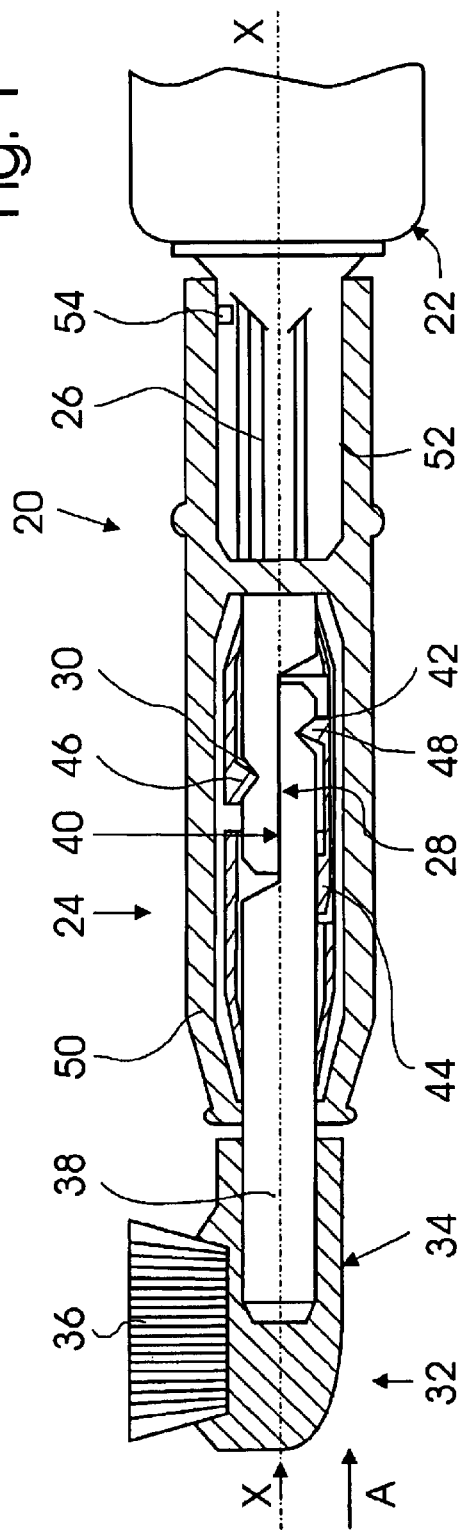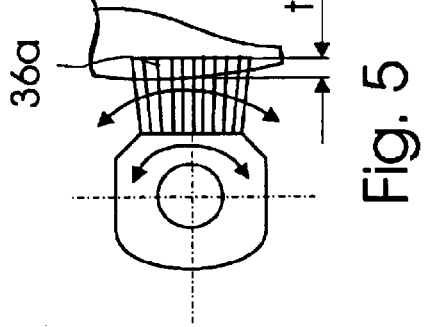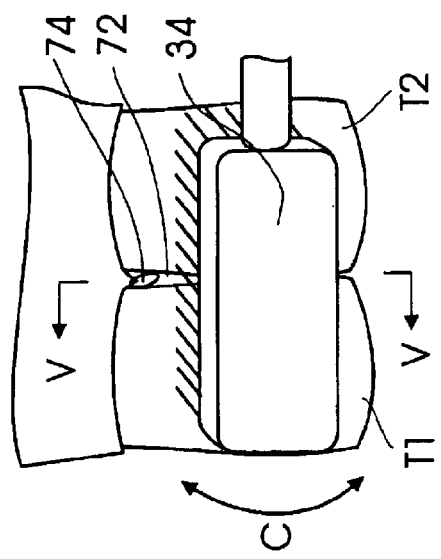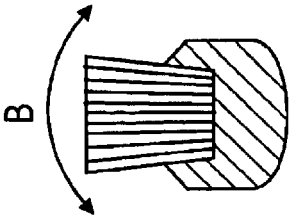

MECHANICALLY-DRIVEN TOOTHBRUSH WITH IMPROVED BRUSHING ACTION

FIELD OF THE INVENTION

The present invention relates to toothbrushes, in particular to mechanically-driven toothbrushes, such as, e.g., electric toothbrushes powered by rechargeable batteries that power an electric motor that in turn drives the toothbrush head.

BACKGROUND OF THE INVENTION

There exist a great variety of tooth-brushing techniques as well as of toothbrushes of both manual and mechanically-driven types. In general, almost all known techniques recommend to brush the outer surfaces of the teeth in the sidewise direction, i.e., in the transverse direction of the teeth. Such cleaning technique does not provide efficient removal of plaque from between the teeth since the bristles will simply slide over the spaces between the adjacent teeth and will not penetrate deep into these spaces. Brushing in a vertical direction of the teeth is recommended only for the inner surfaces of the front teeth.

Almost all existing electrically-driven toothbrushes are designed based on the above concept of sidewise brushing. In terms of movements of the toothbrush head, the existing electric toothbrushes can be divided into brushes with rotary or spinning movement of the brush head and linearly-reciprocating brushy heads. U.S. Pat. No. 5,974,615 issued in 1999 to A. Schwartz-Hartmann, et al. discloses an electric toothbrush, which incorporates a handle and a brush attachment. The handle houses an electric motor. Through a conversion gear and cranking mechanism, rotation of the shaft of the motor is converted into alternating rotations of the shaft, which are transmitted via an intermediate shaft of the brush attachment, connectable to the drive, to the brush head. Through a special cam mechanism the intermediate shaft, and hence, the brush head, also performs stroke motion in the direction transverse to the longitudinal direction of the shaft. The frequency of the stroke movement is higher than the frequency of the rotary movement. In operation, the brush head is oriented with the bristle ends facing the surfaces of the teeth. The stroke movement serves for a poking action of the bristles, which serves to loosen plaque from dental surfaces. The rotary movement serves to wipe away plaque loosened from the dental surfaces. However, because of the rotation of the brush head, the poking motion of the brush is not very efficient. The poking effect of the poking motion is also insufficient since the poking motions are linear in the direction perpendicular to the surfaces of the teeth. In addition, the toothbrush of this type has the same disadvantages as those inherent in electric toothbrushes with the angular transmission, i.e., more complicated structure and shorter service life.

U.S. Pat. No. 5,613,258 issued in 1997 to P. Hilfinger et al. discloses an electric toothbrush with an angularly-driven brush head having a conically-shaped brush intended specifically for removing plaque accumulated between the teeth. Along with disadvantages of the angular transmission, this toothbrush is intended for a specific operation and requires the use of a second general-purpose toothbrush.

OBJECTS OF THE INVENTION

It is an object of the invention to provide a mechanically-driven toothbrush without an angular transmission and with direct connection of the brush head to a driving shaft that performs alternating angular rotations transmitted to the coaxial brush head. Another object of the invention is to provide a toothbrush attachment connectable to a standard mechanically-driven toothbrush handle that incorporates a drive motor with the shaft projecting from the handle and performing alternating angular rotations. Still another object is to provide a mechanically-driven toothbrush with a brush head that imitates movements of a toothpick for efficient removal of plaque from the spaced between the teeth. Another object is to provide a mechanically-driven toothbrush with a brush head intended for brushing in an up-and-down direction over the tooth surface.

BRIEF DESCRIPTION OF THE DRAWINGS

FIG. 1 is a partially-sectional side view of the mechanically-driven toothbrush made in accordance with one embodiment of the invention.

FIG. 3 is a view in the direction of arrow A of FIG. 1.

FIG. 4 is a top view illustrating position of the brush head of the invention during brushing.

FIG. 5 is a sectional view along line V—V of FIG. 4.

SUMMARY OF THE INVENTION

Figure 2:
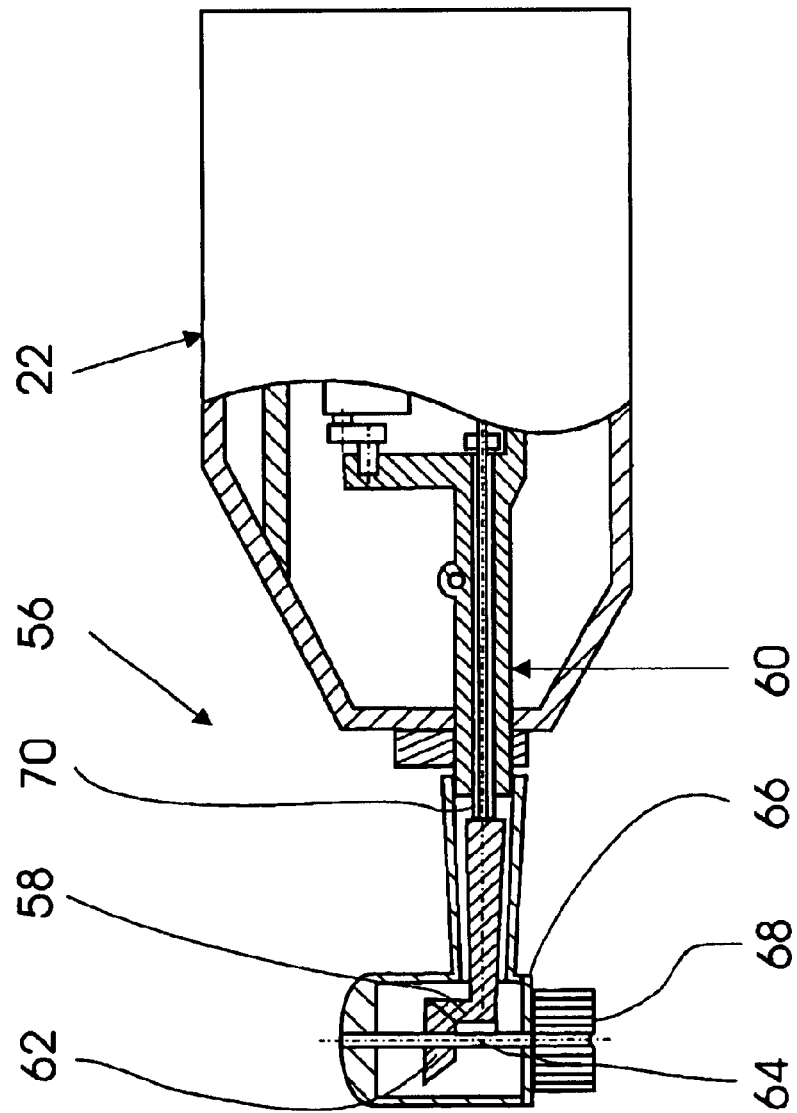
FIG. 2 is a longitudinal sectional view of a known toothbrush attachment disconnected from the standard handle to which the toothbrush attachment of the present invention is connected.

A mechanically-driven toothbrush of the invention consists of a handle that contains a driving motor and a conversion mechanism and a toothbrush attachment, which is removably connected to the handle and contains an intermediate shaft connectable to the output shaft of the conversion mechanism. The handle with the conversion mechanism and the drive motor, e.g., an electric motor driven from a chargeable battery, may comprise a standard, commercially produced unit with the output end of the conversion mechanism performing alternating rotary movements. The toothbrush attachment is made in the form of a conventional toothbrush head without any angular transmission. The tail of the head is connected with the output end of the conversion mechanism by a coupling which has a locking element for engagement with an appropriate locking element on the output end of the conversion mechanism. The connection portion is covered by a protective sleeve that can be removably connected to the front end of the handle. The tail portion of the toothbrush head is coaxial and well balanced with the rotating mechanisms and mass of the handle. In accordance with another embodiment, the protective sleeve can be molded integrally with the housing of the handle and the toothbrush head can be rigidly connected directly to the output end of the conversion mechanism. In operation, the toothbrush head performs alternating rotary movements in the plane perpendicular to the longitudinal axis of the toothbrush, while the user moves the toothbrush up and down in the vertical directions of the teeth. Swinging motions of bristles not only efficiently brush the surfaces of the teeth, but also penetrate into the spaces between the teeth. Efficient removal of the plaque from the spaces between the teeth is achieved due to the fact that motions of the bristles imitate motions of a toothpick when the latter is used for poking the plaque from the intertooth spaces.

DETAILED DESCRIPTION OF THE INVENTION

The applicant has found that, in contrast to a generally used practice of tooth brushing in a sidewise direction, the teeth can be cleaned more efficiently and plaque can be more efficiently removed from spaces between the teeth if the teeth are brushed in an up-and-down direction. Keeping this in mind, the applicant has developed a new mechanically-driven toothbrush which can be easily and inexpensively produced by connecting a simple toothbrush attachment to a standard handle that incorporates a drive and conversion mechanisms.

The invention will be illustrated with reference to an electric toothbrush, which is shown in a partially-sectional side view in FIG. 1. The toothbrush as a whole is designated by reference numeral 20. The electric toothbrush 20 consists of a handle 22, which may be a standard and commercially produced unit, and a toothbrush attachment 24 removably connectable to the output end of the intermediate shaft 26 of the conversion mechanism (not shown) located in the handle 22.

The handle 22 suitable for use in the toothbrush 20 of the embodiment shown in FIG. 1 may comprise a standard unit commercially produced, e.g., by Braun AG, Germany. Details of such a unit are shown and described, e.g., in aforementioned U.S. Pat. No. 5,974,615. Reference to this unit is given herein only as an example and any other standard handle that incorporates a drive motor with alternating rotary motions of the output shaft is suitable for the purposes of the invention. The drive mechanism described in U.S. Pat. No. 5,974,615 consists of a battery-driven electric motor housed in plastic handle and having an output shaft that supports a pinion engaged with a gear wheel, which converts, via a cranking mechanism of the converter, rotations of the shaft of the motor into reciprocating rotations of the intermediate shaft 26 (FIG. 1).

In the embodiment shown in FIG. 1, the end of the intermediate shaft 26 that projects from the handle 22 has a flat 28 and a locking recess 30. A toothbrush head 32 consists of a head portion 34 (e.g., in the form of a conventional manual toothbrush head, with bristles 36) and a tail portion 38, which can be made of metal and has a flat 40 placed onto the flat 28 at the end of the intermediate shaft 26. In a cross section through the flats 28 and 40 both connected portions form a complete circle with the diameter equal to the diameter of the intermediate shaft 26. The tail portion 38 can be rigidly connected to the plastic head 34 by gluing or by fusion so that the head 34 with the bristles 36 form an integral unit with the tail portion 38 and move together with this portion. A recess 42, similar to the recess 30, is formed also on the outer surface of the tail portion 38.

The tail portion 38 and the end of the intermediate shaft 26 are interconnected by means of a coupling sleeve 44, which has on its inner surface snapping projections 46 and 48 that snaps into the respective recesses 30 and 42 formed on the outer surfaces of the intermediate shaft 26 and the tail portion 38 of the toothbrush head 34.

The coupling sleeve 44 and the exposed surfaces of the intermediate shaft 26 and the tail portion 38 are covered by an external protective sleeve 50, which protects the aforementioned exposed surfaces from contamination with toothpaste, pieces of food, plaque, disconnected or broken bristles, etc.

The protective sleeve 50 is removably connected to the front end 52 of the handle 20, e.g., by a bayonet-type connection, which in FIG. 1 is shown conventionally as a pin 54 on the inner surface of the protective sleeve 44 that can be inserted into the L-shaped slot on the surface of the front end 52 and fixed by turning by guiding the pin 52 in the slot (not shown).

The construction of the toothbrush shown in FIG. 1 relates to an embodiment of the invention with interchangeable toothbrush attachments. The attachment 24 shown in FIG. 1 is the one having direct linear connection of the head 34 to the handle 22 so that the head 34 performs alternating rotations integrally with the shaft 26 in a plane perpendicular to an axis parallel to or coaxial to the longitudinal axis X—X of the toothbrush. In the context of the present invention, the term "parallel to" covers the term "coaxial to" as a specific case of the parallel axis which has zero eccentricity with respect to the axis X—X and has a direction coinciding with the longitudinal axis X—X of the handle. Coaxial arrangement of the toothbrush head 34 with respect to the axis X—X is preferable for balanced alternating rotations of the head with minimal level of undesired vibrations.

FIG. 2 is a longitudinal sectional view of a known toothbrush attachment 56 disconnectable from the standard handle 22, to which the toothbrush attachment 24 of the present invention is connected. The toothbrush attachment may be of the type described in aforementioned U.S. Pat. No. 5,974,615 and contains an angular transmission formed by a bevel gear 58 (FIG. 2) attached to the distal end of the intermediate shaft 60 and a bevel gear 62 secured on a transverse axle 64, which is arranged perpendicular to the shaft 60 and supports a round bristle holder 66 with bristles 68. The tail portion 70 of the shaft 60 is the same as the tail portion 38 of the attachment 24 of the invention.

In operation, the intermediate shaft 26 of the conversion mechanism performs alternating rotary motions. When the toothbrush attachment 24 is connected to the shaft 26 via the coupling sleeve 44, the toothbrush head 34 moves integrally with the shaft 26, i.e., performs alternating rotary motions. These motions are more clearly shown by a double-sides arrow B in FIG. 3, which is a view in the direction of arrow A in FIG. 1. These swinging motions occur in the plane perpendicular to the longitudinal axis X—X of the toothbrush 20, while the user moves the toothbrush up and down in the vertical directions of the teeth, as shown in by a double-sided arrow C in FIG. 4, which is a top view illustrating position of the brush head 34 of the invention during brushing. Reference numerals T1 and T2 illustrates an outer side of the adjacent teeth.

Swinging motions of the bristles 36 not only efficiently brush the surfaces of the teeth, but also penetrate into the spaces 72 between the teeth T1 and T2. Efficient removal of the plaque 74 from the spaces 72 between the teeth is achieved due to the fact that motions of the bristles imitate motions of a toothpick when the latter is used for poking the plaque from the intertooth spaces. This is shown in FIG. 5, which is a sectional view along the line V—V of FIG. 4. Reference numeral 36a designate a portion of the bristles 36 which penetrated deep into the space 72 between the teeth to the depth "t".

Figure 6:
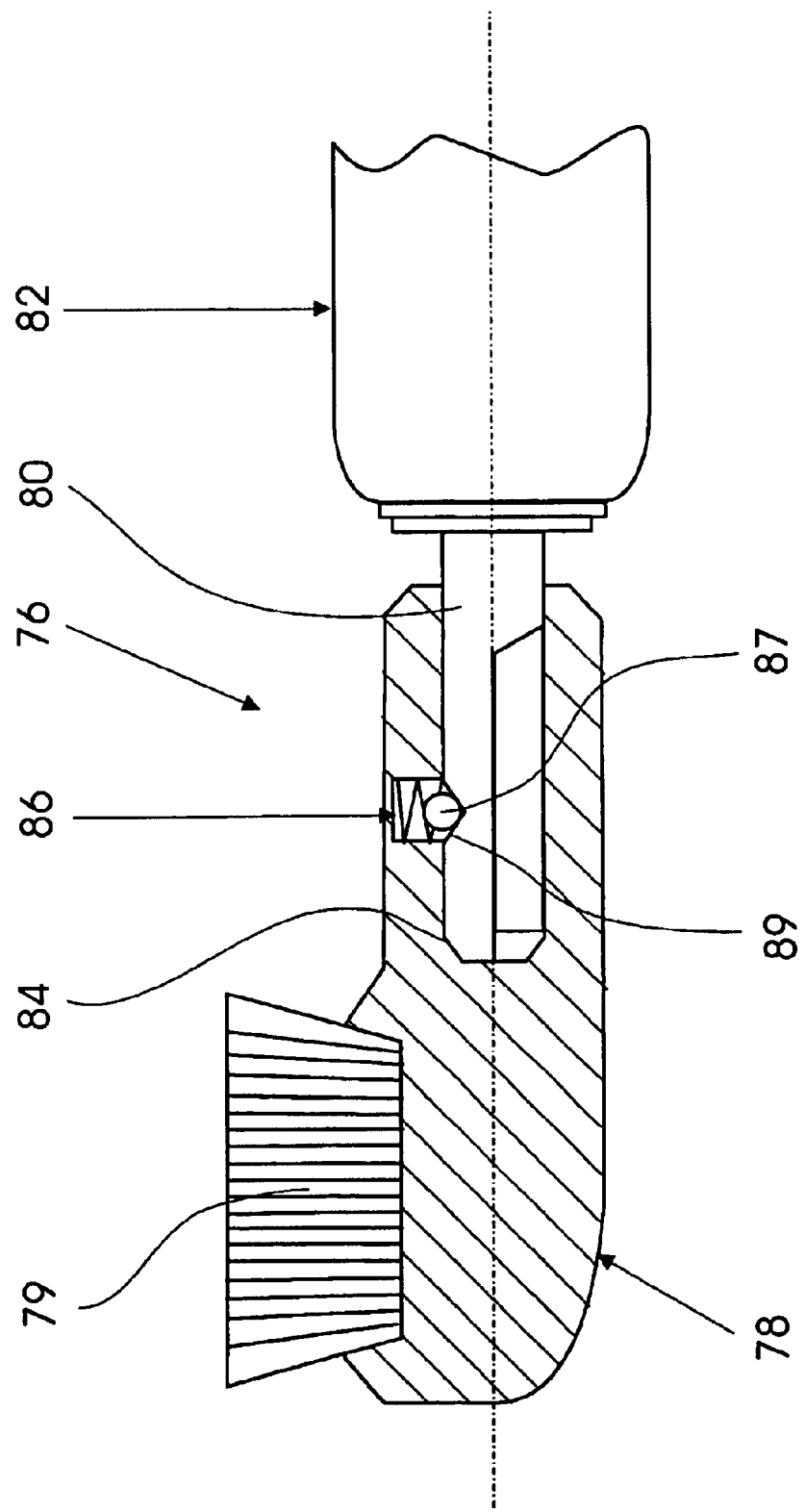
FIG. 6 is a partially sectional side view of the mechanically-driven toothbrush made in accordance with the second embodiment of the invention, in which the toothbrush head is connected directly to the output end of the intermediate shaft projecting from the handle.

FIG. 6 is a partially sectional side view of the mechanically-driven toothbrush 76 made in accordance with the second embodiment of the invention, in which the toothbrush head 78 with bristles 79 is connected directly to the output end of the intermediate shaft 80 projecting from the handle 82. The head 78 has a noncircular opening 84, and the end of the shaft 80, which has a cross-section corresponding to that of the opening 84, is inserted into the opening 84 and is locked therein by a locking mechanism 86, e.g., a spring-loaded ball 87 in the head 78 that snaps into the recess 89 of the shaft 80. The toothbrush of this embodiment operates in the same manner as the one shown in FIG. 1, since the head 78 with the bristles will perform alternating rotary motions together with the shaft 80.

Figure 7:
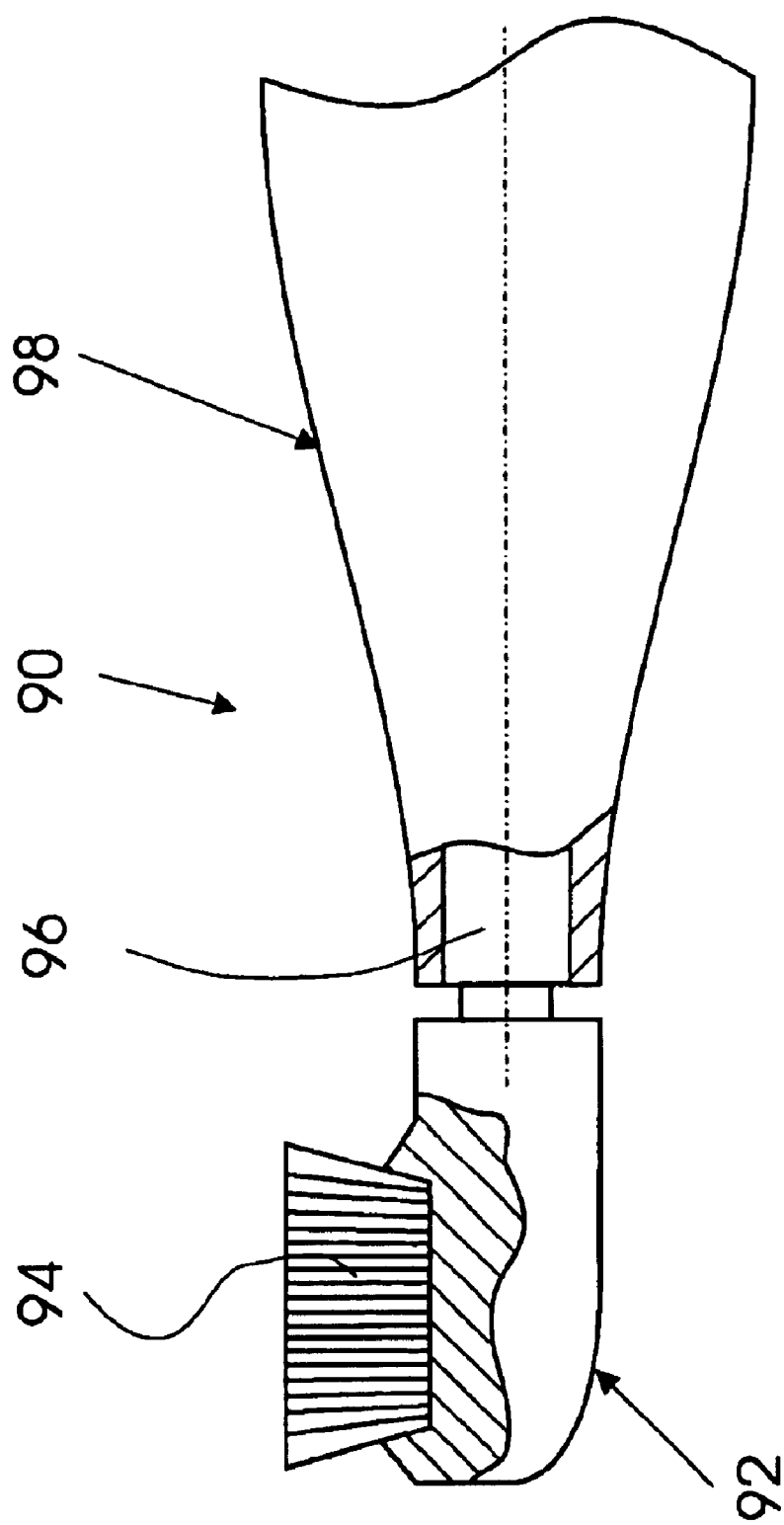
FIG. 7 is a partially sectional side view of the mechanically-driven toothbrush made in accordance with the third embodiment of the invention, in which the toothbrush head is made integrally with the output end of the intermediate shaft projecting from the handle.

FIG. 7 is a partially sectional side view of the mechanically-driven toothbrush 90 made in accordance with the third embodiment of the invention, in which the toothbrush head 92 with the bristles 94 is made integrally with the output end of the intermediate shaft 96 in the handle 98. The toothbrush of this embodiment operates in the same manner as the one shown in FIG. 1, since the head 92 with the bristles will perform alternating rotary motions together with the shaft 96. The embodiment of FIG. 7 is suitable for disposable electric brushes which can be manufactured inexpensively in mass production.

Thus it has been shown that the invention provides a mechanically-driven toothbrush without an angular transmission and with direct connection of the brush head to a driving shaft that performs alternating angular rotations transmitted to the coaxial brush head. In accordance with one embodiment, a toothbrush attachment is connectable to a standard mechanically-driven toothbrush handle that incorporates a drive motor with the shaft projecting from the handle and performing alternating angular rotations. In accordance with another embodiment, the toothbrush head can be connected directly to the output shaft of the conversion mechanism projecting from the handle. In accordance with the third embodiment, the brush head is made integrally with the output shaft of the conversion mechanism projecting from the handle. In all embodiments, the toothbrush head performs alternating rotary motions and thus imitates motions of a toothpick for efficient removal of plaque from the spaced between the teeth. The toothbrush of the invention is convenient for brushing in the up-and-down direction of the teeth.

Although the invention has been described with reference to specific embodiments, it is understood that this embodiment should not be construed as limiting the application of the invention, and various changes and modifications are possible, provided they do not depart from the scope of the patent claims. For example, the brush handles and toothbrush heads may have configurations and shapes different from those shown in the drawings. Drive can be carried out from a battery-charged motor or from a conventional utility power supply, or from a motor different from electric motor, e.g., from a spring-loaded mechanism, etc. Attachments can be connected through mechanisms different from those shown in the drawings. The bristles on the head may have different arrangements, orientations, and combinations. The heads may have a round, rectangular, or oval shape.

What is claimed is:

1. A mechanically-driven toothbrush with improved brushing action, comprising:

a handle which has a longitudinal axis and contains a drive motor with a conversion mechanism for converting rotation of said drive motor into reciprocating rotary motions, said conversion mechanism having an output shaft that is oriented in the direction parallel to said longitudinal axis and projects from said handle and performs said reciprocating rotary motions, and a toothbrush head with bristles; and means for connecting said output shaft to said toothbrush head for transmitting said reciprocating rotary motions to said toothbrush head with rotation around an axis parallel to said longitudinal axis;

said drive motor being an electric motor;

said toothbrush head being connected to said output shaft via a disconnectable attachment, wherein said output shaft has a first connection member, said disconnectable attachment comprising a coupling with a first locking member and with a second locking member, said toothbrush head having a second connection member, said first locking member being connectable to said first connection member of said output shaft, and said second locking member being connectable to said second connection member of said toothbrush head;

said coupling comprising a sleeve having an outer surface and an inner surface, said first locking member and said second locking member comprising snapping projections on said inner surface, and wherein said first connection member and said second connection member comprising recesses engageable with said snapping projections.

2. The mechanically-driven toothbrush of claim 1, further comprising a protective sleeve, which covers said coupling and is connectable to said handle.

3. The mechanically-driven toothbrush of claim 1, wherein said toothbrush is a disposable toothbrush.

\* \* \* \* \*